United States Patent
Herz et al.

(10) Patent No.: US 7,065,528 B2
(45) Date of Patent: Jun. 20, 2006

(54) PROFESSIONAL REFERRAL NETWORK

(76) Inventors: Frederick S. M. Herz, P.O. Box 67, Warrington, PA (US) 18976; Walter Paul Labys, 1445 Lake St., Ogden, UT (US) 84401

( * ) Notice: Subject to any disclaimer, the term of this patent is extended or adjusted under 35 U.S.C. 154(b) by 291 days.

(21) Appl. No.: 10/201,794

(22) Filed: Jul. 24, 2002

(65) Prior Publication Data

US 2004/0019579 A1 Jan. 29, 2004

(51) Int. Cl.
*G06F 17/30* (2006.01)
(52) U.S. Cl. ............................................. 707/10; 707/1
(58) Field of Classification Search .......... 707/1–104.1
See application file for complete search history.

(56) References Cited

U.S. PATENT DOCUMENTS

| | | | | |
|---|---|---|---|---|
| 5,978,767 | A * | 11/1999 | Chriest et al. ................. | 705/1 |
| 6,038,554 | A * | 3/2000 | Vig ............................ | 705/400 |
| 6,691,133 | B1 * | 2/2004 | Rieffanaugh, Jr. ....... | 707/104.1 |
| 6,879,959 | B1 * | 4/2005 | Chapman et al. .............. | 705/2 |
| 2001/0007950 | A1 * | 7/2001 | North et al. .................. | 607/59 |
| 2001/0042004 | A1 * | 11/2001 | Taub ........................... | 705/11 |
| 2002/0010597 | A1 * | 1/2002 | Mayer et al. .................. | 705/2 |
| 2002/0029157 | A1 * | 3/2002 | Marchosky .................... | 705/3 |
| 2002/0038233 | A1 * | 3/2002 | Shubov et al. ................. | 705/8 |
| 2002/0055870 | A1 * | 5/2002 | Thomas ........................ | 705/10 |
| 2002/0065758 | A1 * | 5/2002 | Henley ......................... | 705/37 |
| 2002/0072975 | A1 * | 6/2002 | Steele et al. .................. | 705/14 |
| 2002/0133374 | A1 * | 9/2002 | Agoni et al. ................... | 705/2 |
| 2003/0120511 | A1 * | 6/2003 | Legnini ........................ | 705/2 |
| 2003/0125970 | A1 * | 7/2003 | Mittal et al. ................... | 705/1 |
| 2003/0135128 | A1 * | 7/2003 | Suffin et al. ................. | 600/544 |
| 2003/0149594 | A1 * | 8/2003 | Beazley et al. ................ | 705/2 |
| 2003/0182171 | A1 * | 9/2003 | Vianello ........................ | 705/9 |
| 2003/0182173 | A1 * | 9/2003 | D'Elena et al. ................ | 705/9 |
| 2003/0182178 | A1 * | 9/2003 | D'Elena et al. .............. | 705/11 |
| 2004/0093257 | A1 * | 5/2004 | Rogers et al. ................ | 705/10 |

OTHER PUBLICATIONS

Trewyn, Phill, "Health Care: Bradley Engel, Patiently watching", Business Journal v18n32, Apr. 27, 2001, 2 pages.*

* cited by examiner

*Primary Examiner*—Luke S Wassum
*Assistant Examiner*—Linh Black
(74) *Attorney, Agent, or Firm*—Woodcock Washburn LLP

(57) ABSTRACT

A framework for a system that will allow a professional to vastly extend the web of his referral network, by using a centralized matching system that both protects the privacy of his client, and allows a broad range of outside specialists the opportunity to present themselves. In addition to a database that allows the referring professional to gauge the capabilities of the candidates, the system also includes a bidding system such that candidates can offer a small reward (cash or otherwise) in exchange for being given the work.

13 Claims, 2 Drawing Sheets

Referral Process

Figure 1: Sources of Information
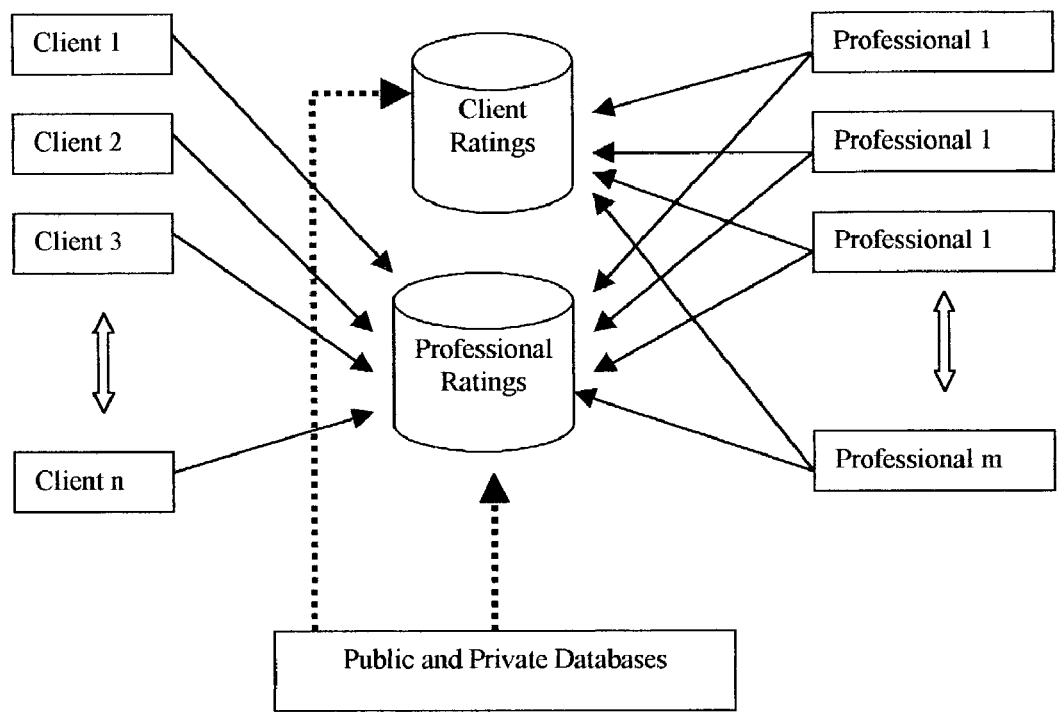

Figure 2: Referral Process
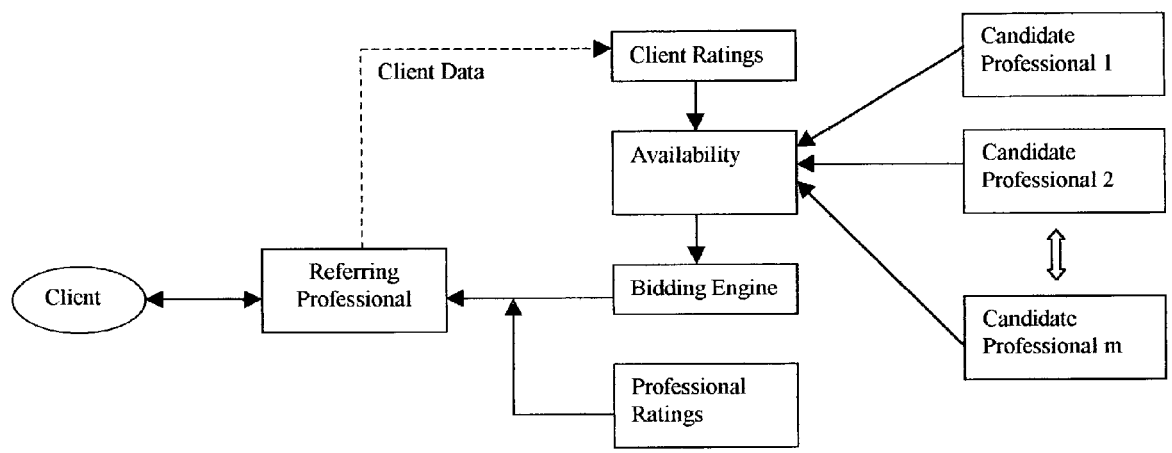

PROFESSIONAL REFERRAL NETWORK

BACKGROUND OF THE INVENTION

Rapidly expanding knowledge and techniques has resulted in increasing sub-specialization. These specialized skills require increasing referral to appropriately trained and experienced physicians. Matching a given clinical problem or multi-disease clinical constellation with the best-qualified clinician/scientists is accordingly increasingly difficult for the general practicing medical community. The presently proposed Professional Referral Network allows greater efficiency and quality in matching disease complexes with the most appropriate specialty care. This referral technique will improve the quality of care for the individual referred patient and for the national quality of medical care, allowing specialty physicians/centers to increase wide spread referral and associated improved quality of medical care at the specialized level as the volume of referred patients grows. The past and current referral mechanism is primarily dependent on referrals to friends and geographic location instead of careful match between disease process and a physician's or surgeon's skills.

SUMMARY OF THE INVENTION

This invention represents an implementation of a Physician Referral Network that involves a system for matching a patient's disease process with optimal medical care. The system has a widely distributed knowledge base about its professionals and clients. The system can be extended to include an increasingly advanced statistical reference technique that allows a broad range of outside specialists.

BRIEF DESCRIPTION OF THE DRAWINGS

FIG. 1 diagrammatically describes the foundations of the system which consist of two databases containing the particular histories, details and experiences of both the clients and professionals.

FIG. 2 describes the preferred implementation, the Referral Network which is made available via a web interface over the Internet.

DETAILED DESCRIPTION OF THE INVENTION

1. Introduction

It is often the case that a professional, lacking the time or capabilities to provide specialized services to his client, will refer the client to some other professional. Traditionally, this has been done through personal contacts and knowledge of local professional resources. Because the passing on of a client is a professional favor, there are often payments (cash or otherwise) made by the specialist to the referring professional. Through the use of automated matching of profiles, one describing the needs of the client and the other describing the skill set of each candidate professional the presently proposed professional referral Network provides much greater efficiency in the referral process, quality of service to the client through receiving of professional services by those professional practitioners who are better suited to particular needs of the client, rewarding through the channel of increased business quantities to those professionals who demonstrate superior skill as well as a means for providing and incentive scheme to those practitioners who are not ideally suited to provide services to certain clients to refer them to one who is.

This invention describes the framework for a system that will allow a professional to vastly extend the web of his referral network, by using a centralized matching system that both protects the privacy of his client, and allows a broad range of outside specialists the opportunity to present themselves. In addition to a database that allows the referring professional to gauge the capabilities of the candidates, the system also includes a bidding system such that candidates can offer a small reward (cash or otherwise) in exchange for being given the work.

2. Creation of Referral Database

As illustrated in FIG. 1, the foundations of the system are two databases containing the particular histories, details, and experiences of both the clients and professionals.

a. Clients' Inputs

Clients may have had experiences (perhaps good, perhaps bad) with particular professionals. They can be polled, and their opinions are used to construct ratings for the pool of available professionals.

b. Professionals' Inputs

Professionals have experiences both with clients, and with each other. Thus, they can be polled on both, with the results being used in the construction of ratings both for clients and for professionals.

c. Public and Private Databases

There are, of course, a multitude of sources, both private and public, that can be culled for information that can be added to the profiles of both individual clients and professionals.

3. Implementation

In the preferred implementation, the Referral Network is made available via a web interface over the Internet. The Network itself (see FIG. 2) consists of the Client Ratings Database, the Professional Ratings Database, an availability list and a referral bid engine. Access to the Network may be limited in various ways (e.g., it may be password protected) so that only approved professionals can interact with it. Approval may depend on such factors as professional accreditation, subscription fees, academic rank and achievement, membership in professional National Societies, honorary society memberships, awards, honors, etc.

Candidate-Side

Specialized professionals looking for clients register their availability with the system. Availabilities may be conditioned on any number of factors, including the nature of the work sought, times available, geographic limitations, etc. Moreover, candidate professionals may restrict the types of clients they are willing to work with (e.g., a doctor may not wish to engage a particularly litigious patient), based on their profiles in the Client Ratings database. All of these various conditions are entered directly into the system by the candidate when he posts his name to the availability list.

The candidate also specifies the fee he is willing to pay for a referral, conditioned on the nature of the client or project. These specifications can be programmed into the bid engine, which uses standard statistical inferential techniques to flexibly alter the bids based on the particular details of each client's situation. Thus, for example, a candidate having a special interest in certain kinds of clients can specify that the fee he is willing to pay for the referral automatically increases when those clients are entered into the system. Or, a professional may be willing to pay higher referral fees in order to gain clientele in geographic proximity to his practice. Of course, all bidding parameters can be specified, so that, for example, the candidate can specify maximum and minimum bids. In more advanced implementations, different candidates' bidding engines can compete directly against each other (as part of an auction) for particularly favorable assignments.

Once the candidate has indicated his availability, his interaction with the system is over: he need only wait for a direct contact from a referring professional, which will be brokered through the system. The candidate does not have to personally screen the clients being entered into the system—and in fact is restricted from viewing potential clients' personal data—the Bidding Engine makes use of his availability conditions to do the screening (and the bidding) for him.

Client-Side

It is often the case that a client will have a specialized problem or project that is beyond the available time or capabilities of his current professional. In such a situation, the professional can turn to the Referral Network, submitting his client's identity and needs to the system.

The system uses the client's identity to extract a profile from the Client Ratings database. This information is then released to the pool of waiting Bidding Engines (but most importantly, not to the candidate professionals themselves). Given the candidates' availability conditions, as well as their pre-specified bidding parameters, the Bidding Engines will calculate how much the candidate is willing to pay for a referral.

In addition to the above 3 parameters, depending upon how expensive the professional services fees are, it may also be useful in the referring professional's decision making process to also have information about the professional fees for the type or amount of professional services offered which can, in turn, be matched to the fee expectations or financial resources or budget constraints of the client. The referring professional is then presented with a screen of the most suitable candidates, including information on (1) their identity, (2) their bids, and (3) their Professional Rating. It is then up to the judgement of the referring professional to choose the most appropriate specialist for his client. If it is a very difficult project or situation, the referring professional may choose a smaller bid but a more qualified candidate. If it is a very simple task, he may choose the candidate offering the highest referral fee.

Example Application: A Physicians' Referral Network

The physicians referral application has some intriguing and exemplary features which are worthy of further explanation. The following general features are useful and appropriate in such an application:

1). A mechanism for patients to provide a collective ratings based assessment of each practitioner by each patient;

2). A collective ratings based quality assessment of each practicioner by the other physicians who have provided referrals to that practitioner;

3). A mechanism for providing barter currency in order to provide a "cashless" net exchange between referring (typically primary) physicians and specialty physicians;

4). A market model to initialize the price values for each type of referral of transaction;

5). A platform with hooks into the patient medial database such that useful and desirable attributes of the patient can be automatically extracted about each patent; and 6). A fuzzy rules based system which is able to match each patient slated for referral with a set of specialists appropriate with the medical profile and/or physician provided request for the type of specialist which is required. If insufficient information is available in the medical profile and/or information provided in the physician's request (if provided), a decision tree is used to prompt the physician for the most relevant additional facts which would need to be provided for the system to make a more accurate and statistically confident match with an appropriate physician The fuzzy rules are ideally initially provided by a human expert (for providing the patient-physician criteria). Based upon the market demand criteria, i.e., the prices offered by various specialists possessing basic matching characteristics, it is possible to refine the rules to prioritize those patient referrals to certain specific positions such as certain types of patients which the physician may tend to refer (e.g., physical location, age, ethnicity, medical conditions or history). Or if it is a new physician, what are the known characteristics of the physician which tend to statistically attract certain types of patients, or what types of patients does the physician already have outside the referral network. Based upon the market-demand which is detected or predicted, priority in the referral/recommendation scheme is provided. In addition, this demand also determines price for that patient based upon a previous test market and, accordingly, the higher paying physician specialist for that similar type of patient. In a variation, the referring physician may discriminate based upon the expected value which each individual, physician, expected to perceive and thus pay for that type of patient referral. The technique for inferring demand for each physician profile and each prospective patient referral given incomplete hard data for each unique matching situation (of attributes of physicians and patients) requires the use of clustering techniques in order to leverage a combination of attributes in cluster space for both physicians and patients as well as the technique for determining an optimal price to just meet but not exceed that demand is disclosed in co-pending patent application entitled. "System for the Automatic Determination of Customized Prices and Promotions". It is further useful to add to the explicit attributes describing each physician, the list of patients for which the physician has the highest demand. Likewise in addition to the explicit attributes of each patient a list of physicians for which the patient possesses the highest demand may be added. These additional attributes may provide additional statistical robustness in accurately predicting demand between each prospective physician-patient match. In addition, each attribute is used as a weighted metric and each physician attribute is adjusted based upon that physician's unique behavior in selecting (and paying) for each type of referral. Patient attributes may also be weighted if the patients selection preferences in physicians are also factored into the matching criteria. This variation represents another variation of the present system.

As suggested above, patients may rate physicians based upon overall quality of treatment and personality as well as a variety of other relevant criteria these values are averaged together and made available at digitally signed credentials to a future referring physician and potentially their patients. Similarly, physicians may rate the physicians to which they refer patients. Important factors (particularly within this medical application domain), whether or not the specialist extended professional courtesies to the referring physician by allowing and encouraging the referring physician to continue treating the patient for the healthcare needs which s/he had originally been treating that patient prior to the referral (and not taking over that treatment role or referring it to a "friend"). Physicians who demonstrate such courtesy, win the trust of the referring physicians by performing good medical services to the patient of that physician (and are thus rated by the referring physician to reflect the same) and are perceived by the patient to provide quality treatment along with personal quality, will receive high ratings by both physician and patients such that the primary physician will approve the transaction if it meets the other primary matching criteria and the referring physician (or another service) will not block referral histories to that doctor in the future. In addition, in the medical application domain, physicians are prohibited by law to receive commissions for referrals. As such, it is possible to use barter currency in the physician transfer of hard currency under any conditions. Busy physicians are thus likely to accrue value at, at least the same rate by referring patients as the value, which they spend in purchasing referrals. Less busy physicians or more highly specialized physicians may accordingly wish to be more selective in choosing more patients which they are likely to be able to later refer in order to be sure that their spending rate doesn't exceed that of their referring activities. The legal restriction on referral fees is not a constraint for legal referrals or most other commercial applications for which the present referral network methodology may be usefully applied. It is also worth mentioning that the present methodology may be an idea/application for peer-to-peer networks due principally to the rapidly changing nature of the directory information or available patients.

In the case of physicians (and likely in other types of professions as well with of course some variations) the referring physician is often a general practicioner (non-specialist) or at least often less specialized than the specialty practicioner to whom the referral is made. In such situations it is often the case that the patient (client) will require on-going medical services from the general practicioner which are typically of a less specialized nature than those for which the referral to the specialist was originally made. In many of these instances, these more general ongoing medical services for the patient can also be provided by the specialist. It is a known fact that even in cases in which the referring physician knows the specialist it is nonetheless a temptation for the specialist to assume these more generalized medical services in addition to the specialty service. This results in antagonism and an associated disincentive for the referring physician to provide similar referrals in the future. In this way referrals can cost the referring physician business. The presently described professional ratings scheme can provide an effective solution to this problem by implementing a form of ratings which indicates the level of professional trust, which previous referring physicians previously experienced in their professional dealings with that specialist as well as (if any) cases of blatant actions or attempts to take business away from referring physicians. As already suggested, this type of problem or other problems resulting from betrayal of trust between professionals who engage in client referral activities are likely to occur in other professional fields and the incentive for professionals to betray the trust of other professionals in this is much greater within the context of the professional referral network in as much as the parties involved are often complete strangers and the amount of business that anyone professional represents to any other is miniscule. Other similar cases in which betrayal of trust may occur may include, for example, attorneys which provide referrals to other attorneys in which the compensation is not a fee but rather is based upon a percentage of those fees ultimately collected by the attorney which is referred. This situation makes it relatively easy for the attorney to not fully disclose to the referred attorney the full amount of the fees, which are collected from the referred client. In this situation (as there may be in other types of professional situations) the potential for different types of professional trust issues including, for example, also the referred attorney taking further business from the referring attorney in the future). Thus depending upon the particular professional, it may be useful to have more than one professional trust rating, which can be provided to each professional by the other professionals with which he does business.

4. Effect of Improving Quality of Specialty Services

The present invention would also improve specialty quality by identifying the best-qualified individuals or groups for a specialty problem. This would also serve to break down regional or institutional specific long-term referral patterns which all to frequently are based on internal political factors instead of objective quality based motivation.

CONCLUSION

This invention describes a straightforward implementation of a Professional Referral Network. In addition is herein disclosed several compelling principal advantages which are achieved through the present system such as improving overall quality of services to clients, rewarding quality performance on the part of practitioners and generally creating an environment wherein practitioners are able to become more focused and specialized with the specialty domains in which they excel. One of the desirable features of the present system which lends to its practical usability and scalability is the fact that all of these very compelling advantages are all the direct result of the system's value exchange which is primary an economically based market driven scheme based upon rewards and incentives which motivate each practitioner to utilize the system's widely distributed knowledge base about its professionals and its clients' needs to perform referral activities which ultimately achieve greater overall benefit to all of the professionals or the network as a whole and thus, ultimately to the client population as well. It can obviously be extended in various ways, including the addition of more advanced statistical inference techniques, or the creation of some sort of cashless currency (or barter) that can be included as part of the bid.

The invention claimed is:

1. A method of providing medical professional referral services, comprising:
   accepting information about a patient's identity and medical needs into a patient database;
   accepting information about the medical specialty, personal characteristics, and referral fees, if any, paid by a candidate physician;
   providing a referring physician access to a matching system that matches a patient to one or more candidate physicians that are available to handle the patient and that determines a referral fee, if any, to be paid to the referring physician; and
   accepting a candidate selection from the referring physician.

2. A method as in claim 1, wherein the matching system protects the patient's identity.

3. A method as in claim 1, comprising the further steps of accepting ratings information from patients and/or referring physicians about candidate physicians and accepting ratings of patients from candidate physicians.

4. A method as in claim 1, comprising the further steps of accepting referral fee bids from candidate physicians for a particular patient and selecting the highest referral fee bid using an auction system.

5. A method as in claim 1, comprising the step of representing said referral fees as input into a cashless barter system between referring physicians and candidate physicians.

6. A system for providing medical professional referral services, comprising:
 a patient database that accepts and stores information about a patient's identity and medical needs;
 a candidate physician database that accepts and stores information about the medical specialty, personal characteristics, and referral fees, if any, paid by a candidate physician;
 a matching system that matches a patient to one or more candidate physicians that are available to handle the patient and that determines a referral fee, if any, to be paid to the referring physician; and
 an interface to said matching system that accepts a candidate selection from the referring physician.

7. A system as in claim 6, wherein said interface is a web enabled interface that connects said matching system to the Internet.

8. A system as in claim 6, wherein the matching system protects the patient's identity.

9. A system as in claim 6, wherein the candidate physician database accepts and stores ratings information from patients and/or referring physicians about candidate physicians and the patient database accepts and stores ratings of patients from candidate physicians.

10. A system as in claim 6, wherein said matching system comprises an auction system that accepts referral fee bids from candidate physicians for a particular patient and selects the highest referral fee bid.

11. A system as in claim 6, wherein said matching system comprises a cashless barter system that barters referral fees between referring physicians and candidate physicians.

12. A system as in claim 6, wherein said matching system comprises a fuzzy rules based system that matches patients to candidate physicians in accordance with rules provided by a human expert.

13. The system of claim 6, wherein said matching system weights attributes of the patient and the candidate physicians based on established selection preferences.

* * * * *